United States Patent
Abe et al.

(10) Patent No.: US 8,384,380 B2
(45) Date of Patent: Feb. 26, 2013

(54) MAGNETIC RESONANCE IMAGING APPARATUS AND MAGNETIC RESONANCE IMAGING METHOD

(75) Inventors: Takayuki Abe, Tokyo (JP); Hiroyuki Takeuchi, Tokyo (JP); Tetsuhiko Takahashi, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 601 days.

(21) Appl. No.: 12/663,939

(22) PCT Filed: Jun. 25, 2008

(86) PCT No.: PCT/JP2008/061544
§ 371 (c)(1),
(2), (4) Date: Dec. 10, 2009

(87) PCT Pub. No.: WO2009/004963
PCT Pub. Date: Jan. 8, 2009

(65) Prior Publication Data
US 2010/0156418 A1 Jun. 24, 2010

(30) Foreign Application Priority Data
Jul. 2, 2007 (JP) .................................. 2007-173620

(51) Int. Cl.
*G01V 3/00* (2006.01)
(52) U.S. Cl. ........................................ 324/307; 324/309
(58) Field of Classification Search .................. 324/307, 324/309, 314; 600/410
See application file for complete search history.

(56) References Cited

U.S. PATENT DOCUMENTS

| 6,272,369 | B1 * | 8/2001 | Tan .................................. 600/410 |
| 6,483,307 | B2 * | 11/2002 | Ookawa .......................... 324/309 |
| 6,781,375 | B2 * | 8/2004 | Miyazaki et al. ............... 324/314 |
| 8,040,134 | B2 * | 10/2011 | Abe et al. ......................... 324/309 |
| 2003/0144587 | A1 | 7/2003 | Ma et al. |

FOREIGN PATENT DOCUMENTS

| JP | 4-256730 | 9/1992 |
| JP | 10-314136 | 12/1998 |
| JP | 2003-230549 | 8/2003 |

OTHER PUBLICATIONS

Abe, Takayuki, et al. , "B1 Insensitive na Shibo Yokusei Koka o Mokuteki to shita Multiple Fatsat Pulse no Kaihatsu," Japanese Society of Radiological Technology Sokai Gakujutsu Taikai Yokoshu, Feb. 20, 2007, $63^{rd}$, p. 208.

* cited by examiner

*Primary Examiner* — Louis Arana
(74) *Attorney, Agent, or Firm* — Cooper & Dunham LLP

(57) ABSTRACT

In order to stably obtain an even fat-suppressed image without reduction of an imaging efficiency and without being affected by unevenness of irradiation magnetic field of an RF pulse, when an imaging sequence having a first sequence part for suppressing a signal from a desired component of an examinee by applying a CHESS pulse and a second sequence part for measuring an echo signal from the examinee is repeated, the flip angle of the CHESS pulse is changed at plural times. In the case of multi-slice imaging, the flip angle of the CHESS pulse is changed in at lest two slice imaging.

12 Claims, 8 Drawing Sheets

FIG. 8
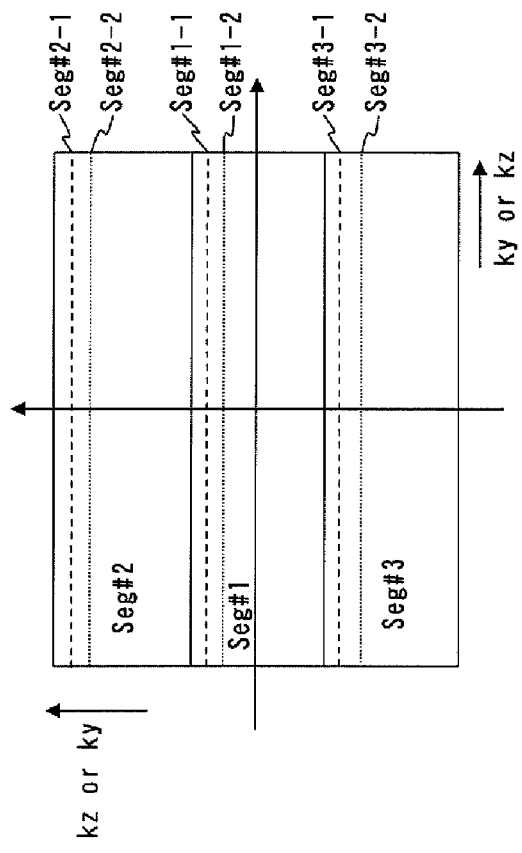
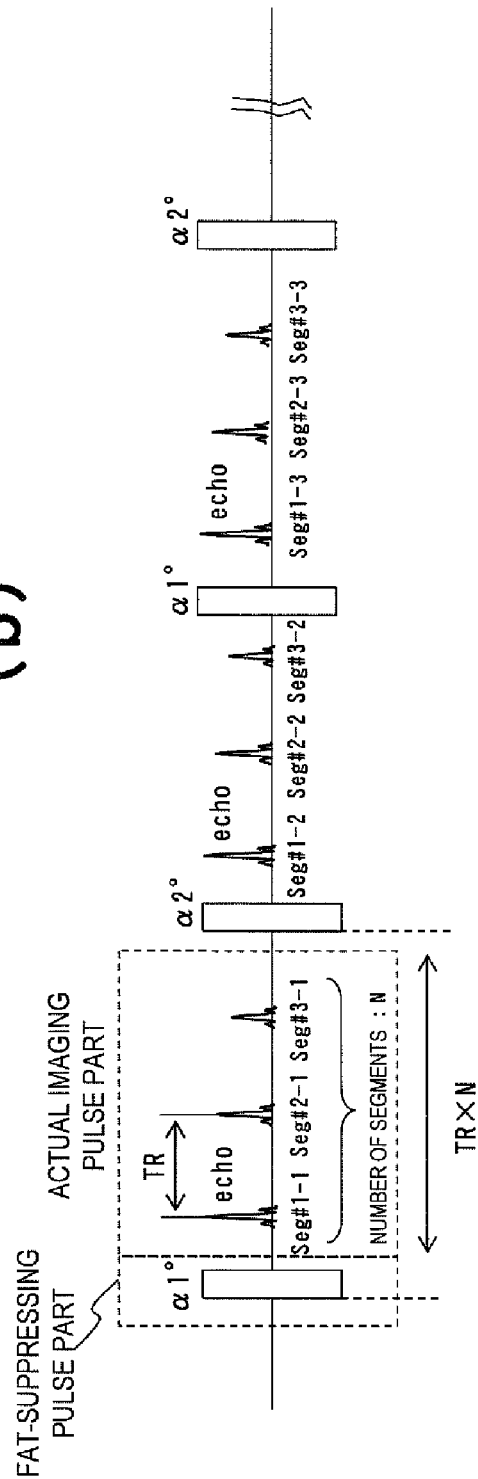

MAGNETIC RESONANCE IMAGING APPARATUS AND MAGNETIC RESONANCE IMAGING METHOD

TECHNICAL FIELD

The present invention relates to a nuclear magnetic resonance imaging (hereinafter referred to as "MRI") apparatus and MRI method for measuring a nuclear magnetic resonance (hereinafter referred to as "NMR") signal from hydrogen, phosphorus or the like in an examinee to image a density distribution of nucleus, a relaxation time distribution or the like, and particularly to a fat inhibiting technique using chemical shift.

BACKGROUND ART

When a biochemical tissue is placed in an even magnetic field space (B0, B0 direction is defined as z) in an MRI apparatus, the magnetic moments of atomic nucleus spins of tissue composing molecules make precession movement around the B0 direction at the natural resonance frequency of each spin. When these spins are exposed to a magnetic field (irradiated radio frequency magnetic field B1) having a frequency near to the resonance frequency from a direction perpendicular to the B0 direction, the net magnetic moment M is rotated (excited) toward the x-y plane, and a net transverse magnetic moment occurs. Thereafter, when the irradiated radio frequency magnetic field B1 is turned off, the magnetic moment being excited is returned (relaxed) to its original state while emitting energy (NMR signal). At this time, the MRI apparatus detects the emitted NMR signal (echo signal) and executes signal processing on the NMR signal to obtain an image of the biochemical tissue.

The MRI apparatus as described above generally images hydrogen protons. Hydrogen is contained in many different molecules in a living body and exists in a living body, so that the resonance frequency of hydrogen protons is slightly different among molecules because the interaction in molecular level is different. For example, in 1.5T MRI apparatus, an echo signal occurring from hydrogen protons in fatty molecules has a frequency which is lower by about 224 Hz than the frequency of an echo signal occurring from hydrogen protons in water molecules. By using this resonance frequency difference, only an image of an echo signal from desired molecules can be obtained.

With respect to clinical imaging, it is required in some cases to image only a signal from water molecules. As a technique for satisfying such a requirement is known a CHESS method of suppressing an echo signal from hydrogen protons of fatty molecules (hereinafter abbreviated as "fatty protons") by applying a CHESS pulse before actual imaging (non-patent document 1). According to this well-known technique, a radio frequency magnetic field (hereinafter referred to as "RF") pulse having a fixed magnetic field intensity (in this case, a flip angle is 90° having the resonance frequency of fatty protons, which is a CHESS pulse, is applied to a living body to selectively excite the fatty protons, and then a crusher gradient magnetic field pulse is applied. Accordingly, transverse magnetization of the fatty protons which are selected and excited by the CHESS pulse is subjected to phase dispersion, and the magnetization of the fatty protons is vanished immediately before the actual imaging, whereby the signal from the fatty protons is suppressed.

According to this fatty signal suppressing technique using this CHESS method, if the irradiation intensity of the RF pulse generated by the CHESS pulse is spatially homogenous with respect to fat which is spatially broadly distributed, some fixed suppressing effect can be obtained. However, the chess method has still have an unsolved problem that unevenness of suppression of the fatty signal would occur if the irradiation intensity is spatially uneven. Particularly, it has been reported that the spatial unevenness of the irradiation intensity of the RF pulse is remarkable under high magnetic field (1.5T or more).

Non-patent document 2 discloses a method using an adiabatic type inverting pulse to solve incomplete fat suppression due to unevenness of irradiation intensity of the RF pulse as described above. The method described in the non-patent document 2 does not control a general RE pulse based on only amplitude modulation, but controls an RF pulse which is subjected to frequency modulation (phase modulation) as well as amplitude modulation. A combination of a hyperbolic secant function for amplitude modulation and a hyperbolic tan function for frequency modulation is generally used as modulation functions. Accordingly, a magnetization equilibrium state under the state that desired spins are inverted can be established, and all the desired spins can be kept to be uniformly inverted.

Non-patent document 1: A. Hasse, J. Frahm, et al: H1 NMR chemical shift selective (CHESS) imaging. Phys. Med. Biol. 30, 341 (1985)

Non-patent document 2: "Design of Adiabatic pulses for Fat-Suppression using Analytic Solutions of the Bloch Equation". MRM 37: 793-801 (1997).

DISCLOSURE OF THE INVENTION

Problem to be Solved by the Invention

However, with respect to the method disclosed in the non-patent document 2, it is required to start an actual imaging sequence after lapse of a time required until a state under which longitudinal magnetization of inverted fatty protons is equal to zero (null state) is established, that is, an inversion recovery time (T1: T1 time of fat at 1.5T is equal to about 150 to 170 ms). That is, it is required to start the actual imaging sequence at the timing at which the longitudinal magnetization of fatty protons is set to the null state, which causes extension of the total imaging time or reduction of the maximum number of slices which can be imaged within the same repetitive time (TR). Therefore, this method has consequently an unsolved problem that the imaging efficiency is lowered. Furthermore, the method disclosed in the non-patent document 2 indispensably needs a waiting time defined by the inversion recovery time, and it is unsuitable for short TR imaging like T1 enhanced imaging.

Furthermore, in the short TR imaging like the T1 enhanced imaging, the CHESS pulse is repetitively applied at a short interval, and thus magnetization of fatty protons reaches a stationary state. Therefore, a certain amount of longitudinal magnetization of fatty protons is left under the stationary state. Therefore, a certain level of echo signal from fatty protons is detected, and thus a certain intensity of fat remains on the image.

Therefore, the present invention has been implemented in view of the foregoing problem, and has an object to obtain an even fat-suppressed image stably without causing reduction of the imaging efficiency and also without being affected by unevenness of irradiated magnetic field of an RF pulse.

Means of Solving the Problem

In order to attain the above object, an MRI apparatus and an MRI method according to the present invention are constructed as follows. That is, a flip angle of a CHESS pulse is changed when an imaging sequence is repeated. Specifically, they are characterized in that when an imaging sequence having a first sequence unit for applying a CHESS pulse to suppress a signal from a desired component of an examinee and a second sequence unit for measuring an echo signal from the examinee is repeated, a flip angle of the CHESS pulse is changed at plural times.

Effect of the Invention

According to the MRI apparatus and the MRI method of the present invention, the flip angle of the first sequence unit to be executed is controlled to be changed as a pulse sequence for suppressing a signal from specific atomic nucleus spins, whereby an even fat-suppressed image can be stably obtained without reduction of an imaging efficiency and also without being affected by unevenness of irradiation intensity of an RF pulse. Furthermore, even when the repetitive application time interval of the CHESS pulse is short, a homogenous fat-suppressed image can be stably obtained.

BRIEF DESCRIPTION OF THE DRAWINGS

FIG. 8 is a diagram showing segment measurement in a second embodiment of the present invention.

Figure 1:
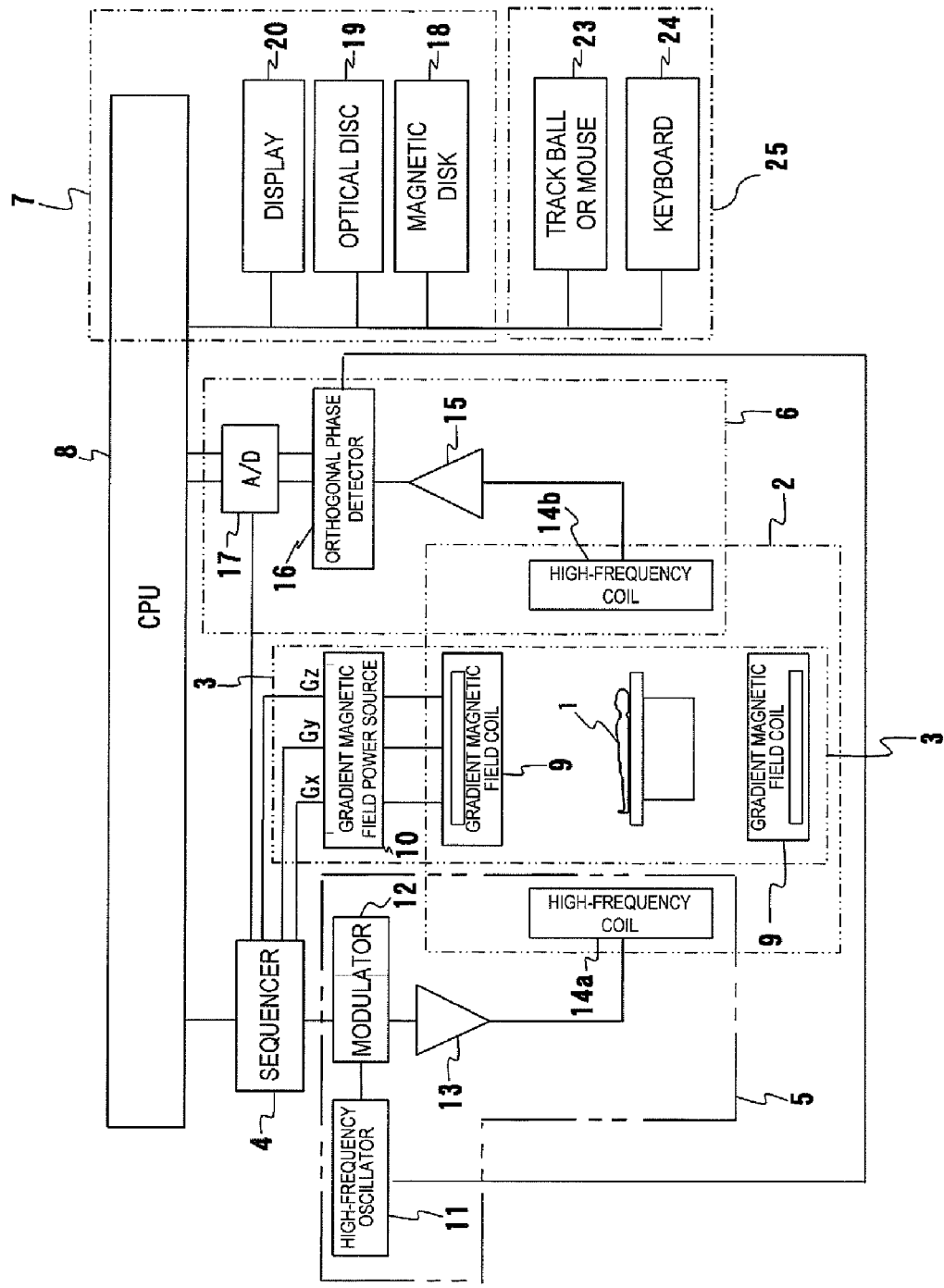
FIG. 1 is a block diagram showing the overall construction of an embodiment of an MRI apparatus according to the present invention.

DESCRIPTION OF REFERENCE NUMERALS 1 examinee, 2 magnetostatic field generating system, 3 gradient magnetic field generating system, 4 sequencer, 5 transmission system, 6 reception system, 7 signal processing system, 8 central processing unit (CPU), 9 gradient magnetic field coil, 10 gradient magnetic field power source, 11 high-frequency oscillator, 12 modulator, 13 high-frequency amplifier, 14a high-frequency coil (transmission coil), 14b high-frequency coil (reception coil), 15 signal amplifier, 16 orthogonal phase detector, 17 A/D converter, 18 magnetic disc, 19 optical disc, 20 display, 23 track ball or mouse, 24 keyboard, 51 gantry, 52 table, 53 housing, 54 processing device

BEST MODE FOR CARRYING OUT THE INVENTION

A preferred embodiment of an MRI apparatus of this invention will be described with reference to the accompanying drawings. In all the figures for describing the embodiment of this invention, elements having the same functions are represented by the same reference numerals, and the repetitive description thereof is omitted.

First, the overall construction of an example of the MRI apparatus according to this invention will be briefly described with reference to FIG. 1. FIG. 1 is a block diagram showing the overall construction of the embodiment of the MRI apparatus of this invention. The MRI apparatus obtains a tomogram of an examinee by using the NMR phenomenon, and as shown in FIG. 1, the MRI apparatus comprises an magnetostatic field generating system 2, a gradient magnetic field generating system 3, a transmission system 5, a reception system 6, a signal processing system 7, a sequencer 4 and a central processing device (CPU) 8.

The magnetostatic field generating system 2 generates an even magnetostatic field in a direction perpendicular to the body axis of the examinee 1 in a space surrounding the examinee 1 in the case of a vertical magnetic field system, and also generates an even magnetostatic field in the body axis direction in the case of a horizontal magnetic field system. A permanent magnet type, normal conduction type or a superconductive type magnetostatic field generating source is disposed around the examinee 1.

The gradient magnetic field generating system 3 comprises gradient magnetic field coils 9 wound in three axis directions of X, Y and Z of the coordinate system (the coordinate system at rest) of the MRI apparatus, and a gradient magnetic field power source 10 for driving each of the gradient magnetic field coils.

The gradient magnetic field generating system 3 drives the gradient magnetic field power source 10 for each coil according to an instruction from a sequencer 4 described later to apply gradient magnetic fields Gx, Gy, Gz in the three axis directions of X, Y and Z. Under the imaging operation, a slice-direction gradient magnetic field pulse (Gz) is applied in a direction perpendicular to a slice plane (imaging section) to set the slice plane for the examinee 1, and a phase encode direction gradient magnetic field (Gp) and a frequency encode direction gradient magnetic field pulse (Gf) are applied in the other two directions which are perpendicular to the slice plane and also perpendicular to each other, thereby encoding position information in the respective directions into the echo signal.

The transmission system 5 irradiates the examinee 1 with an RF pulse to induce nuclear magnetic resonance in atomic nucleus spins of atoms constituting a biochemical tissue of the examinee 1, and it comprises a high-frequency oscillator 11, a modulator 12, a high-frequency amplifier 13 and a high-frequency coil (transmission coil) 14a at the transmission side. A high-frequency pulse output from the high-frequency oscillator 11 is subjected to amplitude modulation in the modulator 12 at a timing based on an instruction from the sequencer 4, and the amplitude-modulated high-frequency pulse is amplified by a high-frequency amplifier 13, and then supplied to the high-frequency coil 14a disposed in the neighborhood of the examinee 1, whereby the examinee 1 is irradiated with the RF pulse.

The reception system 6 detects an echo signal (NMR signal) which is emitted due to the nuclear magnetic resonance of the atomic nucleus spins constituting the biochemical tissue of the examinee 1, and it comprises a high-frequency coil (reception coil) 14b at the reception side, a signal amplifier 15, an orthogonal phase detector 16 and an A/D converter 17. A response echo signal of the examinee 1 which is induced by electromagnetic waves irradiated from the high-frequency coil 14a at the transmission side is detected by the high-frequency coil 14b disposed in the neighborhood of the examinee 1, amplified by the signal amplifier 15 and then divided into orthogonal signals of two systems by an orthogonal phase detector 16 at a timing based on an instruction from the sequencer 4. Each of the signals is converted to a digital amount by the A/D converter 17, and transmitted to a signal processing system 7. The digital data of the echo signal will be hereinafter referred to as echo data.

The sequencer 4 is control means for repetitively applying an RF pulse and a gradient magnetic field pulse at a predetermined pulse sequence, and it is operated under the control of CPU 8 and transmits various instructions required for data collection of tomograms of the examinee 1 to the transmission system 5, the gradient magnetic field generating system 3 and the reception system 6. Furthermore, in the MRI apparatus of this invention, the sequencer 4 has means which can perform measurement while varying the output of the high-frequency magnetic field pulse.

The signal processing system 7 performs various kinds of data processing and display, saving, etc. of processing results, and it has an external storage device such as an optical disc 19, a magnetic disk 18 or the like, and a display 20 comprising CRT or the like. When data are input from the reception system 6 into CPU 8, CPU 8 executes processing such as signal processing, image re-construction, etc., and it displays a tomogram of the examinee 1 as a processing result and records the tomogram into the magnetic disk 18 or the like of the external storage device. Furthermore, CPU 8 has a memory corresponding to K space therein and stores echo data. The description that the echo data are arranged in the K space means that the echo data are written and stored in the memory. The echo data written in the memory corresponding to the K space is called as K space data.

The operating unit 25 inputs various kinds of control information of the MRI apparatus and control information of the processing executed in the signal processing system 7, and it comprises a track ball or a mouse 23, and a keyboard 24. This operating unit 25 is disposed in proximity to the display 20, and an operator interactively controls various kinds of processing of the MRI apparatus through the operating unit 25 while watching the display 20.

In FIG. 1, the high-frequency coil 14a and the gradient magnetic field coils 9 at the transmission side are disposed in the magnetostatic field space of the magnetostatic field generating system 2 in which the examinee 1 is inserted, and arranged so as to face the examinee 1 in the case of the vertical magnetic field system or so as to surround the examinee 1 in the case of the horizontal magnetic field system. Furthermore, the high-frequency coil 14b at the reception side is disposed so as to face the examinee 1 or surround the examinee 1.

Hydrogen atomic nucleus (proton) as a main constituent material of the examinee is known as clinically-popular imaging target nuclear species of the present MRI apparatus. By imaging information concerning the spatial distribution of the proton density or the spatial distribution of the relaxation time of the excitation state, the configuration or function of a head region, an abdominal region, extremities or the like of a human body is imaged two-dimensionally or three-dimensionally.

A fat-suppressing imaging sequence for suppressing an echo signal from fatty protons is installed as an imaging sequence in the MRI apparatus according to this invention, and CPU 8 calculates the optimum flip angle of the CHESS pulse to suppress the echo signal from the fatty protons according to an imaging condition input from the operator, etc.

First, a fat-suppressing imaging method using the fat-suppressing imaging sequence having the CHESS pulse will be described with reference to FIGS. 2 and 3.

Figure 2:
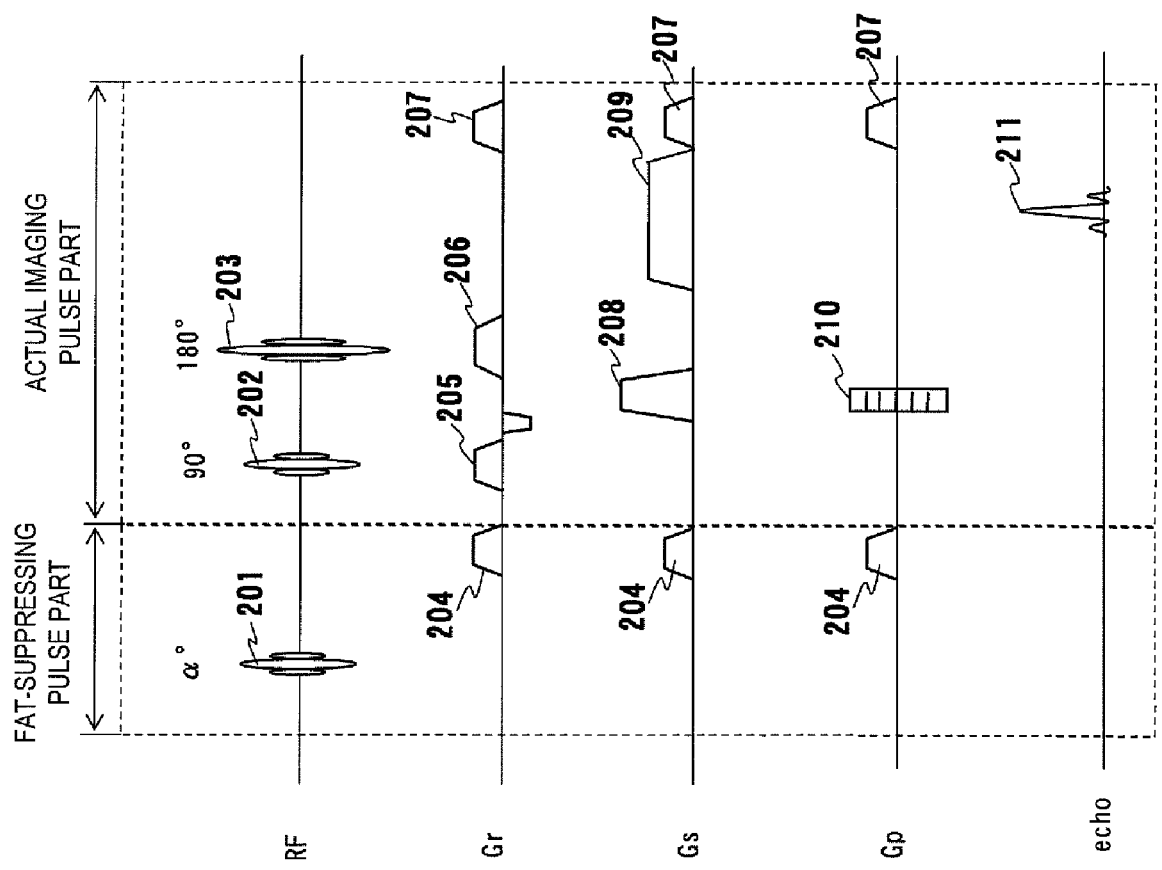
FIG. 2 is a diagram showing a sequence chart of a fat-suppressing imaging sequence provided with a CHESS pulse.

FIG. 2 is a sequence chart showing an example of the fat-suppressing imaging sequence for implementing the fat-suppressing imaging method executed in the MRI apparatus. The fat-suppressing imaging sequence has a fat-suppressing pulse part (first sequence part) for suppressing an echo signal from fatty protons by using a CHESS pulse, and an actual imaging pulse part (second sequence part) for measuring an echo signal to obtain an image of the examinee in which a signal from a fatty tissue is suppressed. The RF pulse (RF), the slice gradient magnetic field (Gs), the phase encode gradient magnetic field (Gp) and the reading gradient magnetic field (Gr) are controlled by the sequencer 4, and applied at timings described in a sequence chart, so that the echo signal (echo) is measured in the actual imaging pulse part by the reception system 6.

The fat-suppressing pulse part is a pulse sequence part for vanishing magnetization of fatty protons in an imaging area. The CHESS pulse 201 for selectively exciting the fatty protons is applied in a non-slice selection style, that is, with no application of the slice gradient magnetic field. The flip angle of the CHESS pulse is set to a predetermined angle) ($\alpha°$). A spoiler gradient magnetic field pulse 204 for phase-dispersing transverse magnetization of the fatty protons excited by the CHESS pulse is applied subsequently to the CHESS pulse.

The spoiler gradient magnetic field pulse 204 of the fat-suppressing pulse part shown in FIG. 2 is applied to the three axes of Gr, Gs and Gp, however, it may be applied to at least one axis. In the case of multi-slice imaging, the CHESS pulse is applied in the non-slice selection style, and thus the CHESS pulse is applied so as to contain all of these slices. The magnetization of the fatty protons in the imaging area is vanished by the fat-suppressing pulse part as described above after the fat-suppressing pulse part, that is, before the actual imaging pulse part.

The actual imaging pulse part is a pulse sequence part for measuring an echo signal to obtain an image of the examinee. Any pulse sequence is possible. FIG. 2 shows an example using a well-known spin echo sequence as the actual imaging sequence. In this spin echo sequence, 90° exciting pulse 202, 180° re-convergence pulse 203, slice selection gradient magnetic field 205, 206, reading gradient magnetic field 208, 209 and phase encode gradient magnetic field 210 are applied to measure an echo signal 211. After the measurement of the echo signal, the spoiler gradient magnetic field 207 is applied to the three axes. By the actual imaging pulse part as described above, the echo signal for the image of the examinee is measured under the state that the magnetization of fatty protons is vanished by the fat-suppressing pulse part disposed just before the actual imaging pulse part. As a result, a fat-suppressed image in which the signal from the fatty tissue is suppressed can be obtained.

Figure 3:
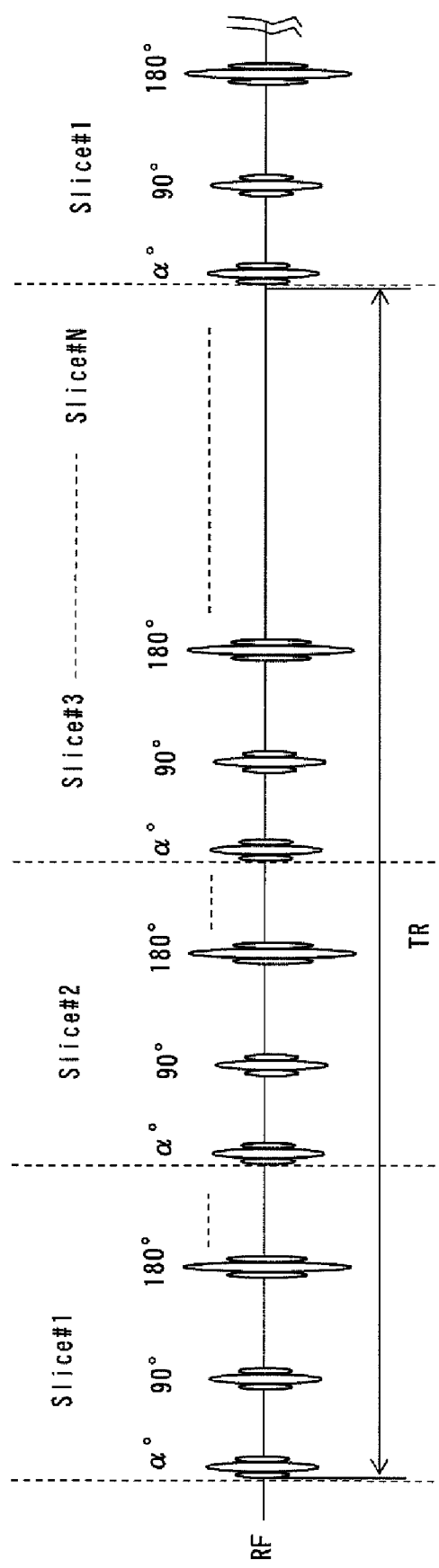
FIG. 3 is a diagram showing a pulse sequence of an RF pulse portion when the fat-suppressing imaging sequence of FIG. 2 is multi-sliced.

FIG. 3 shows an example of the sequence chart when the basic construction of the fat-suppressing imaging sequence shown in FIG. 2 is applied to multi-slice imaging. The sequencer 4 controls the multi-slice imaging on the basis of this sequence chart. In FIG. 3, only the sequence of an RF pulse is shown. With respect to the other gradient magnetic field pulse sequence and echo signal sequence, the sequences shown in FIG. 2 are repeated every slice. In the multi-slice imaging, the fat-suppressing imaging sequence of FIG. 2 is repeated by the frequency corresponding to the number of slices (N in this case) within one repeat time (TR), whereby the fat-suppressed image of each sliced section is picked up. That is, the fat-suppressing pulse part and the subsequent actual imaging pulse part are repeated every TR/N time. In each fat-suppressing pulse part, the CHESS pulse of a predetermined flip angle $\alpha°$ is simultaneously applied to all the slices in the non-slice selection style. In each actual imaging pulse part, only one slice is imaged for each TR/N time, and also the slice is changed every TR/N time. The fat-suppressed image of each slice is obtained by the multi-slice imaging using the fat-suppressing imaging sequence as described above.

First Embodiment

Next, a first embodiment of the MRI apparatus and the MRI method according to the present invention will be described. According to this embodiment, in the multi-slice imaging using the fat-suppressing imaging sequence in which the number of slices is set to 1 or more, the CHESS pulse is applied while the flip angle of the CHESS pulse is not fixed, but varied. Accordingly, a homogenous fat-suppressed image can be obtained even when the irradiation intensity of the RF pulse is uneven to some degree. The other portions are the same as the multi-slice imaging of FIG. 3. Therefore, the description of the same portions is omitted, and only different portions will be described hereunder with reference to FIG. 4.

Figure 4:
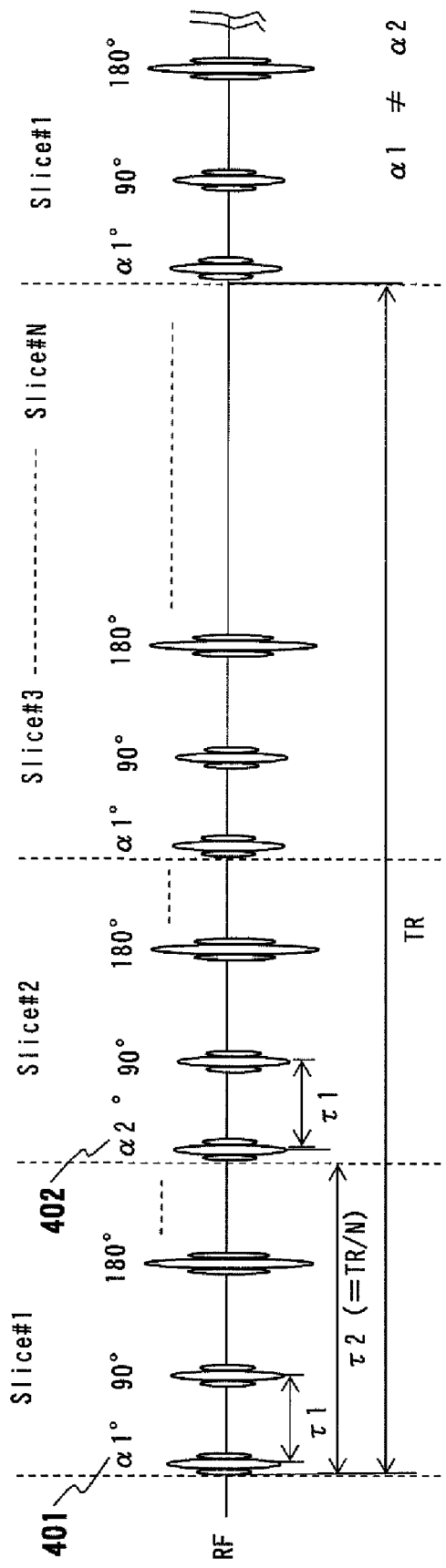
FIG. 4 is a diagram showing the pulse sequence of the RF pulse portion of the fat-suppressing imaging sequence according to a first embodiment of the present invention.

FIG. 4 shows a sequence chart of multi-slice imaging using the fat-suppressing imaging sequence of this embodiment in which the number of slices is set to 1 or more. The sequencer 4 controls the fat-suppressing imaging on the basis of this sequence chart. In FIG. 4, only the sequence of the RF pulse is shown as in the case of FIG. 3. Each CHESS pulse is a non-slice selection RF pulse as in the case of FIG. 3. With respect to the other gradient magnetic field pulse sequence and echo signal sequence, the sequences shown in FIG. 2 are repeated every slice.

In the fat-suppressing imaging sequence of this embodiment, the plural flip angles are regularly repeated every time the fat-suppressing imaging sequence is repeated. Or, the plural flip angles may be randomly repeated. For example, as shown in FIG. 4, the sequencer 4 controls the flip angle of the CHESS pulse in the fat-suppressing pulse part so that the flip angle is alternately varied between $\alpha 1$ and $\alpha 2$ ($\alpha 1 \neq \alpha 2$) every time the CHESS pulse is applied. That is, the flip angle of the CHESS pulse is alternately varied every slice imaging sequence in such a manner that the flip angle of the CHESS pulse applied in the fat-suppressing imaging sequence of one slice is set to $\alpha 1$, the flip angle of the CHESS pulse applied in the fat-suppressing imaging sequence of the next slice is set to $\alpha 2$, and the flip angle of the CHESS pulse applied in the fat-suppressing imaging sequence of the subsequent slice is set to $\alpha 1$, $\alpha 2$, $\alpha 1$, $\alpha 2$, .... Alternatively, flip angles $\alpha 1$, $\alpha 2$, $\alpha 3$, ... of three kinds or more are regularly or randomly changed every slice imaging sequence. Or, the flip angle of the CHESS pulse may be changed at plural times regularly or randomly, not every time the fat-suppressing imaging sequence is repeated, but also when the fat-suppressing imaging sequence is repeated. Accordingly, an even fat-suppressed image can be obtained even when the irradiation intensity of the RF pulse is uneven to some degree. The reason for this and a method of determining the flip angles $\alpha 1$ and $\alpha 2$ will be described later.

As a result, as shown in FIG. 4, the CHESS pulse is non-slice selection, and thus the CHESS pulse of the fat-suppressing pulse part is applied to the whole slice area every fat-suppressing imaging sequence. In a case where the number of slices is even, it seems that the flip angle of the CHESS pulse is equal to $\alpha 1$ when only even-numbered slice images are viewed and it is equal to $\alpha 2$ when only odd-numbered slice images are viewed. However, for all the slices, each of the CHESS pulses of $\alpha 1$, $\alpha 2$ are alternately applied.

Next, the fat-suppressing imaging processing will be described with reference to FIG. 5.

Figure 5:
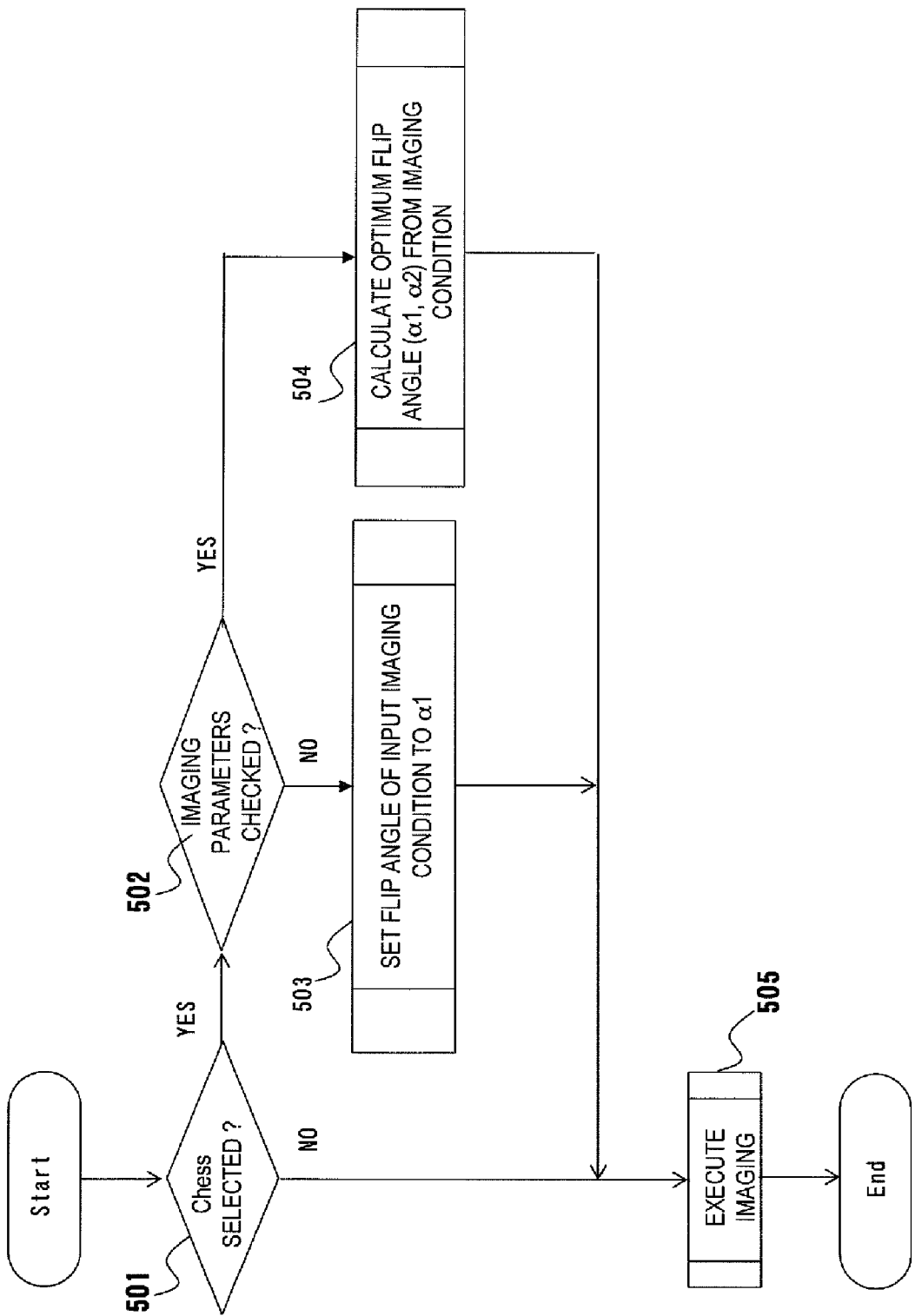
FIG. 5 is a flowchart showing an example of a processing flow according to the first embodiment of the present invention.

FIG. 5 shows the processing flow of switching the CHESS pulse control in accordance with the value of TR (repeat time)/N (number of slices) and obtaining an even fat-suppressed image without reducing the time efficiency even when the irradiation intensity of the RF pulse is uneven to some degree in the imaging operation based on the fat-suppressing imaging sequence using the CHESS method. This embodiment is suitable for a case where TR/N is reduced as in the case of attainment of a T1 enhanced image. Therefore, when the value of TR/N is smaller than a predetermined threshold value, the CHESS pulse control is applied as the method of this embodiment. Each step of this processing flow is stored as a program in the magnetic disk 18 in advance, and it is read and executed in CPU 8 as occasion demands. The details of the respective processing steps will be described hereunder.

In step 501, an operator selects the fat-suppressing imaging sequence using the CHESS method, and sets necessary imaging parameters. For example, the operator selects the fat-suppressing imaging sequence using the CHESS method in a menu displayed on the display 20 through the operating unit 25, and additionally sets imaging parameters such as the repeat time (TR), the number of slices (N), etc. which are required for the pulse sequence concerned.

In step 502, CPU 8 checks whether the imaging parameters set by the operator are suitable for the execution of the fat-suppressing imaging sequence of this embodiment. For example, it is checked whether TR/N is shorter than a predetermined time as a determination criterion, and 100 ms or a value before or after 100 ms (for example, 80 to 120 ms) may be selected as a rough indication of the predetermined time. When TR/N is shorter, the processing goes to step 504, and when TR/N is longer, the processing goes to step 503.

When TR/N is longer than the predetermined time in step 503, CPU 8 reads out a program for executing the CHESS pulse control of the same flip angle from the magnetic disk 18, and executes the program. On the basis of the program for executing this CHESS pulse control, CPU 8 sets the flip angle of the CHESS pulse to $\alpha$, and determines the output amplitude of the CHESS pulse from this flip angle $\alpha$. Then, the processing goes to step 505.

When TR/N is shorter than the predetermined time in step 504, CPU 8 reads out the program for executing the CHESS pulse control of this embodiment from the magnetic disk 18, and executes the program. On the basis of the program for executing the CHESS pulse control of this embodiment, CPU 8 calculates the flip angles $\alpha 1$, $\alpha 2$ of the CHESS pulse for minimizing M(2) according to expression (3) described later by using TR (repeat time) and N (number of slices) input from the operator and a known T1 value of fat (about 200 ms in the case of 1.5T) as input values. CPU 8 determines the output amplitude of the CHESS pulse from $\alpha 1$, $\alpha 2$, and then the processing goes to step 505.

When the operator instructs to start the fat-suppressing imaging sequence in step 505, on the basis of the determined output amplitude of the CHESS pulse, the sequencer 4 executes the multi-slice imaging using the fat-suppressing imaging sequence under the CHESS pulse control of the same flip angle or this embodiment, and measures the echo signal every slice. That is, in the case of the CHESS pulse control of the same flip angle, the output amplitude of the CHESS pulse, that is, the flip angle is set to be fixed without being dependent on the slice, and the fat-suppressing imaging sequence shown in FIG. 3 is executed. Alternatively, in the case of the CHESS pulse control of this embodiment, the fat-suppressing imaging sequence shown in FIG. 4 in which the flip angle of the CHESS pulse is alternately varied between α1 and α2 every slice imaging operation is executed. CPU 8 executes the image re-constructing processing by using the measured echo signal, and obtains the fat-suppressed image of the examinee every slice.

The above-described processing is the processing of the fat-suppressing imaging based on the fat-suppressing imaging sequence using the CHESS method, whereby the homogenous fat-suppressed image is obtained stably without reducing the time efficiency even when the irradiation intensity of the RF pulse is uneven to some degree. Furthermore, in the multi-slice imaging, the CHESS pulse is applied for the short repeat time of TR/N (the rough indication of "short" is TR/N< (T1/2 of fat)), however, in such a case, an even fat-suppressed image can be also stably obtained irrespective of unevenness of the irradiation intensity of the RF pulse.

Next, the method of determining the flip angles α1, α2 of the CHESS pulse according to this embodiment will be described.

According to the Bloch equation, when the longitudinal magnetization Mz is disturbed from the equilibrium state by excitation based on an RF pulse, it is relaxed by some time constant (T1 relaxation time). Here, when the time from application of a CHESS pulse 401 (flip angle α1) till a 90° excitation pulse of actual imaging is represented by τ1, the time between CHESS pulses is represented by τ2 (=TR/N), and the T1 relaxation time of fatty protons excited by the CHESS pulse is represented by T12 as shown in FIG. 4, the longitudinal magnetization Mz(2) of fatty protons after application of the CHESS pulses 401 (flip angle α1) and 402 (flip angle α2) and just before the 90° excitation pulse in the actual imaging pulse part can be calculated as follows.

First, the longitudinal magnetization Mz(1) of fatty protons just before 90° pulse in the actual imaging pulse part just after the application of the CHESS pulse 401 (flip angle α1) is represented by the expression (1).

$$M(1) = 1 - (1 - M(0) \times \cos\alpha 1) \times \exp(-\tau 1/T1) \quad \text{expression (1)}$$
$$= M(0) \times \cos\alpha 1 \times \exp(-\tau 1/T1) +$$
$$(1 - \exp(-\tau 1/T1))$$

Here, M(0) represents initial magnetization, and is represented by the expression (2).

$$M(0) = 1 - \exp(-\tau 2/T1) \quad \text{expression (2)}$$

τ2 represents the time interval between the CHESS pulses, and it corresponds to TR/N.

The longitudinal magnetization Mz(2) of fatty protons just before 90° pulse in the actual imaging pulse part just after subsequent application of the CHESS pulse 402 is represented by the expression (3).

$$M(2) = 1 - (1 - M(1) \times \cos\alpha 2) \times \exp(-\tau/T1) \quad \text{expression (3)}$$
$$= M(0) \times \cos\alpha 1 \times \cos\alpha 2 \times \exp(-2\tau 1/T1) +$$
$$(1 - \exp(-\tau 1/T1)) \times \cos\alpha 2 \times$$
$$\exp(-\tau 1/T1) + (1 - \exp(-\tau 1/T1))$$

The 90° pulse and the 180° pulse in the actual imaging pulse part are slice-selection pulses. When some slice is noted, they are applied at a longer interval (=TR) than the application interval (=TR/N) of the CHESS pulse, and thus the action thereof is neglected in this case.

Figure 6:
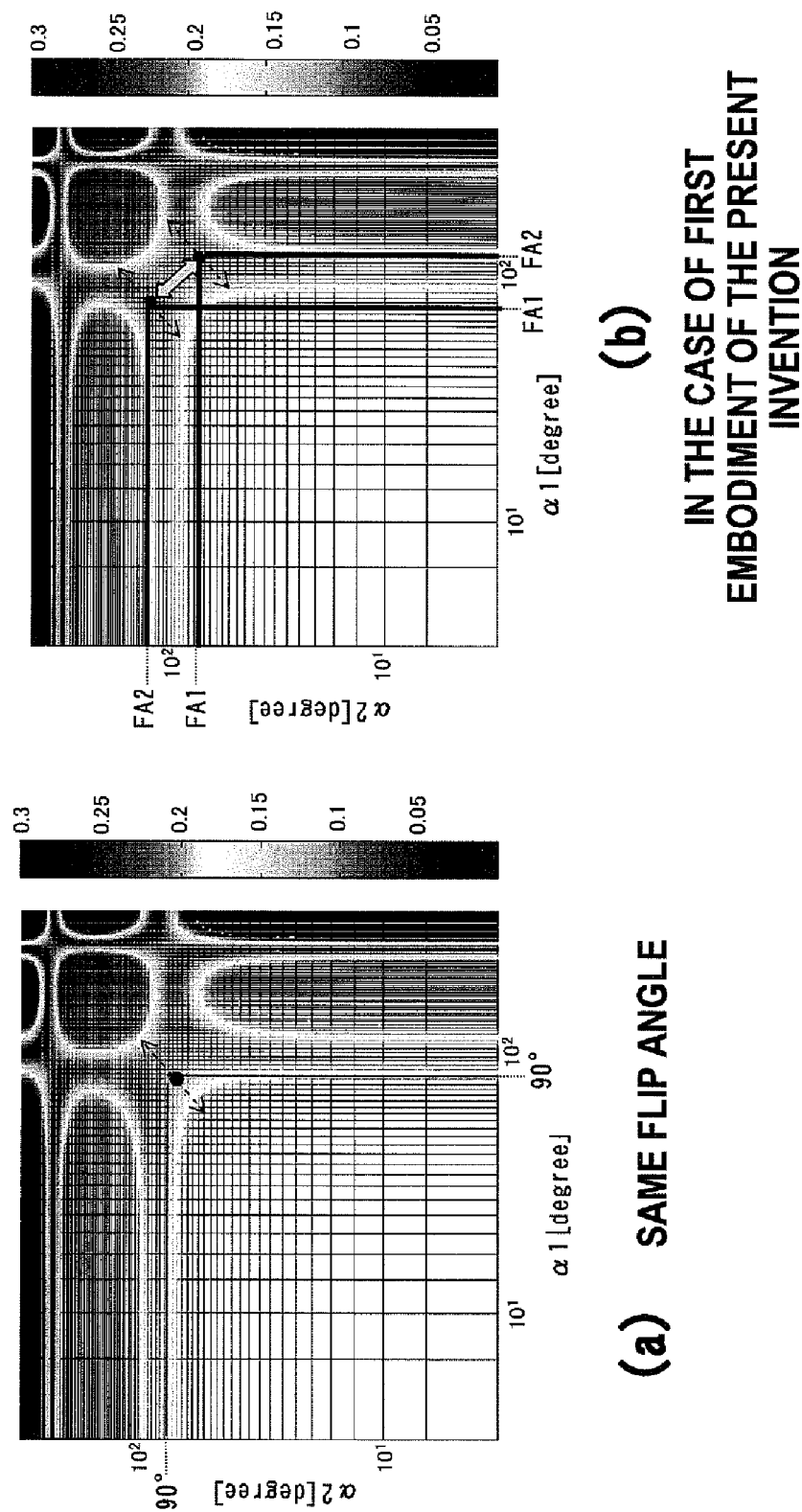
FIG. 6 is a state transition diagram viewed in a residual longitudinal magnetization M(2) map of fat in the case of a CHESS pulse having the same flip angle (a) and in the case of the first embodiment of this invention (b).

FIG. 6 shows an example of the distribution of M(2) to the combination of the respective CHESS pulses α1 and α2. This is an example of the calculation under the condition: T1 of fat=200 ms and TR/N=100 ms.

The example of FIG. 6(a) corresponds to the control of the flip angle α1=α2=90°. The value of a dot shown in FIG. 6(a) is equal to a high value of 10% (the rate of longitudinal magnetization to the initial value) under the state of M(2). Furthermore, when the irradiation intensity of the RF pulse is uneven, dispersion occurs in each CHESS pulse α1, α2. Variation trajectories of M(2) when the irradiation intensity of the RF pulse varies within ±50% are indicated by arrows in FIG. 6(a). It is understood from FIG. 6(a) that many variation trajectories are contained in an area where the M(2) value is equal to a high value in the range from 10 to 15%. That is, in the case of the same flip angle, this means that a signal from fat remains at a high signal intensity of 10 to 15% when the irradiation intensity of the RF pulse is uneven.

On the other hand, in the embodiment shown in FIG. 6(b), the construction of the two flip angles (FA) in which M(2) is minimum, that is, α1=FA1, α2=FA2 or α1=FA2, α2=FA1 is set (for example, FA1=70°, FA2=110°). Arrows of FIG. 6(b) show variation trajectories of M(2) when the irradiation intensity of the RF pulse is uneven within ±50%. The CHESS pulse repeats the transition of α1→α2, α2→α1 at a fixed interval, and thus the longitudinal magnetization is alternately changed between states at two points as indicated by a heavy arrow every time the CHESS pulse is applied. It is understood from FIG. 6(b) that many arrow areas are contained in an area in which the value of M(2) is small, and thus the CHESS pulse control can reduce M(2) even when the irradiation intensity of the RF pulse is uneven.

Figure 7:
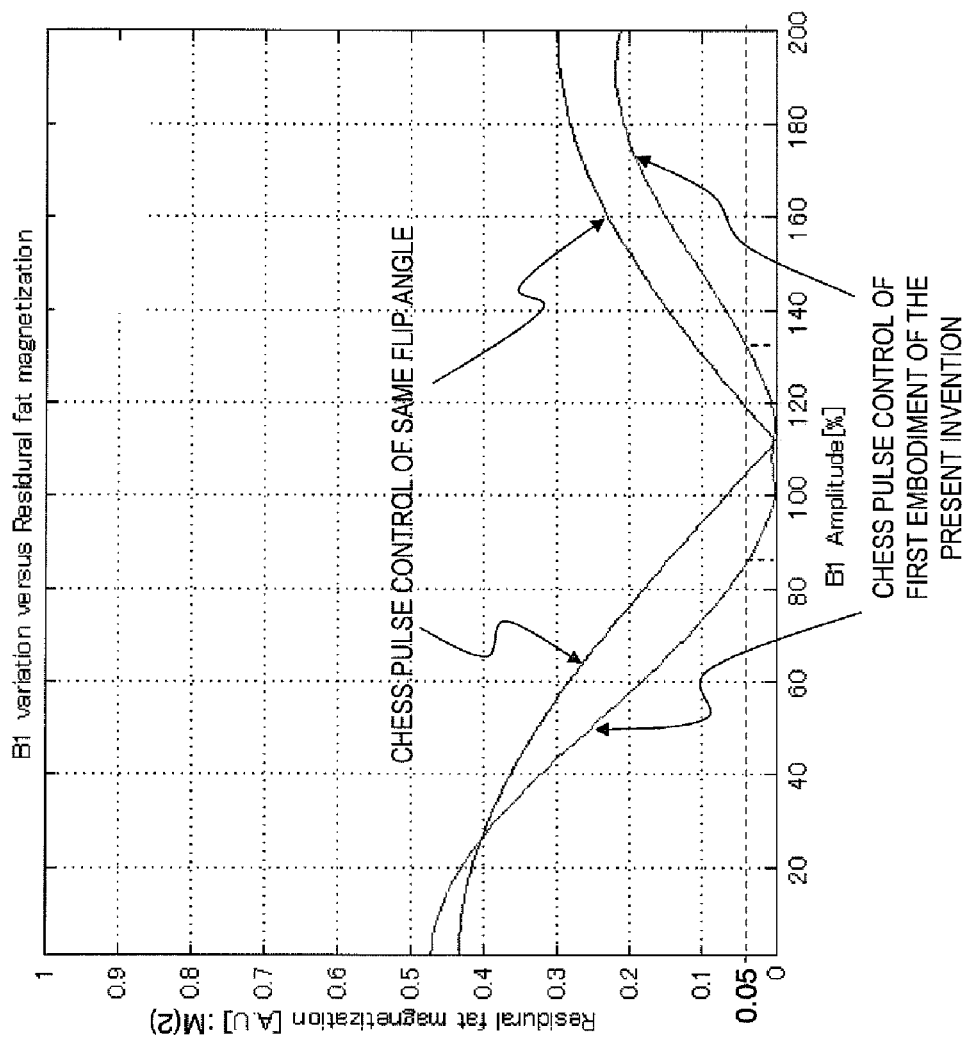
FIG. 7 is a diagram showing an example of a residual longitudinal magnetization M(2) graph of fat with respect to irradiation intensity variation of the RF pulse.

FIG. 7 shows a profile of the residual longitudinal magnetization M(2) of fat protons to the unevenness of the irradiation intensity of the RF pulse of ±100%. From FIG. 7, it is understood that the CHESS pulse control of this embodiment can suppress M(2) to the unevenness of the irradiated magnetic field of the RF pulse of ±15% so that M(2) is reduced to be less than 0.05.

As is apparent from the foregoing description, according to the CHESS pulse control of this embodiment, the CHESS pulse α2 is applied before the magnetization excited by the CHESS pulse α1 has been recovered (M(0)≠1), so that the fat signal can be stably suppressed in a broad irradiation intensity range of the RF pulse as the composite action of the CHESS pulse α1 and the CHESS pulse α2.

As described above, according to this embodiment, in the multi-slice imaging in which the number of slices is equal to 1 or more, by changing the flip angle of the CHESS pulse, that is, varying the flip angle of the CHESS pulse which is repetitively executed, the longitudinal magnetization of fatty protons can be stably suppressed without being affected by unevenness of irradiation intensity even when the irradiation intensity of the RF pulse is uneven. As a result, the influence of the unevenness of the irradiation intensity of the RF pulse can be reduced, and an even fat-suppressed image can be stably obtained.

Particularly, in the multi-slice imaging, the CHESS pulse is applied at the short repeat time TR/N (<T1/2 of fat)). However, in such a case, fat protons are suppressed from reaching the stationary state, and thus the fat signal can be stably and evenly suppressed.

Second Embodiment

Next, a second embodiment will be described. In this embodiment, the flip angle of the CHESS pulse is varied in segment measurement. That is, the K space is divided into plural segments, the actual imaging pulse part measures each echo signal belonging to plural segments, and the fat-suppressing pulse part applies CHESS pulses having different flip angles. Only the different points from the first embodiment described above will be hereunder described, the description of the same parts is omitted, and this embodiment will be described with reference to FIG. 8.

FIG. 8 shows the flip angle control of the CHESS pulse in the segment measurement of this embodiment.

FIG. 8(a) shows an example in which the K space is divided into segments of N (=3) in the phase encoded direction (ky direction). The center portion containing the origin of the K space (that is, a low area in the ky direction of the K space) is set to a segment 1 (Seg#1), and two areas at both the ends (that is, high areas in the ky direction of the K space) are set to a segment 2 (Seg#2) and a segment 3 (Seg#3), respectively. Furthermore, it is indicated that measured echo signals (Seg#1-1, Seg#1-2, ..., Seg#2-1, ..., Seg#3-1, ...) are filled from the +side to the –side in the ky direction in each segment. This embodiment is not limited to the three-segment division, but it may be applied to segment division of two segments or four or more segments. Furthermore, the dividing direction is not limited to the phase encode direction (ky direction), but it may be the slice encode direction (kz direction) in the 3D imaging.

FIG. 8(b) shows a sequence chart of the fat-suppressing imaging sequence of this embodiment. The sequencer 4 suppresses the fat suppressing imaging of this embodiment on the basis of this sequence chart. This sequence chart represents only the echo signals, and each RF pulse and each gradient magnetic field pulse in the actual imaging pulse part are omitted from the illustration. This is because in this embodiment, the fat-suppressing pulse part is the same as the first embodiment described above, and any pulse sequence of the actual imaging pulse part may be used. In this embodiment, the K space is subjected to segment measurement, and thus this embodiment is suitable for high-speed pulse sequence. For example, a 2D/3D gradient echo sequencer of short TR is suitably used. In FIG. 8(b), it is assumed that the gradient echo sequence is used as the pulse sequence of the actual imaging pulse part.

In the actual imaging pulse part of this embodiment, as shown in FIG. 8(b), the echo signal is measured every segment, and also a different echo signal is measured every fat-suppressing imaging sequence. Specifically, in the first actual imaging pulse part, a first echo signal Seg#1-1 of Seg#1, a first echo signal Seg#2-1 of Seg#2, and a first echo signal Seg#3-1 of Seg#3 are measured. In the next second actual imaging pulse part, a second echo signal Seg#1-2 of Seg#1, a second echo signal Seg#2-2 of Seg#2, and a second echo signal Seg#3-2 of Seg#3 are measured. In the next third actual imaging pulse part, a third echo signal Seg#1-3 of Seg#1, a third echo signal Seg#2-3 of Seg#2, and a third echo signal Seg#3-3 of Seg#3 are measured, and so on.

As described above, in each actual imaging pulse part, echo signals belonging to each segment are respectively measured from the +side to the –side in the ky direction, and in the actual imaging pulse part, the echo signal to be measured is changed every segment and the segment measurement is executed. That is, when the number of segment is represented by N, in each actual imaging pulse part, one or two or more echo signals are measured every segment, and the total N or more echo signals are measured, and the imaging time of the actual imaging pulse part. When the repeat time of the gradient echo sequence is represented by TR, the imaging time of the actual imaging pulse part is equal to TR*N or more.

The actual imaging pulse part as described above is repeated together with the fat-suppressing pulse part. The flip angles of $\alpha 1$ and $\alpha 2$ are alternately repeated like such that the flip angle of the CHESS pulse applied on the basis of the fat-suppressing pulse is changed like $\alpha 1 \rightarrow \alpha 2 \rightarrow \rightarrow \alpha 1 \rightarrow \alpha 2 \rightarrow, \ldots$. Alternatively, three or more flip angles may be regularly or randomly repeated. Accordingly, an even fat-suppressed image can be stably obtained without reducing the time efficiency even when the irradiation intensity is uneven to some degree.

As described above, according to this embodiment, as compared with the fat-suppressed measurement using the segment division in combination of the CHESS pulse control of the same flip angle, by the segment measure in which the flip angle of the CHESS pulse is varied, an even fat-suppressed image can be stably obtained without being affected by the unevenness of the irradiation intensity of the RF pulse even when the irradiation intensity of the RF pulse is uneven.

The embodiments of the present invention have been described, however, various modifications may be made to the present invention without limiting the present invention to the above embodiments. For example, fatty protons are described as nuclear species targeted by the CHESS pulse in the embodiments. However, hydrogen protons in water molecules may be used under chemical shift imaging. Furthermore, the flip angles of the CHESS pulse are alternatively changed. However, the flip angle may be regularly or randomly changed among three or more flip angles.

The invention claimed is:

1. A magnetic resonance imaging apparatus comprising measurement control means configured to measure an echo signal necessary for image reconstruction from an examinee by repeating a predetermined imaging sequence, the imaging sequence having a first sequence part configured to apply a CHESS pulse to suppress a signal from a desired component of the examinee, and a second sequence part configured to measure the echo signal, wherein the measurement control means cyclically or randomly changes a flip angle of the CHESS pulse at plural times within a plurality of flip angles in repetition of the imaging sequence.

2. The magnetic resonance imaging apparatus according to claim 1, wherein the measurement control means regularly repeats plural flip angles every repetition of the imaging sequence.

3. The magnetic resonance imaging apparatus according to claim 2, wherein the measurement control means applies the CHESS pulse in a non-slice selection style.

4. The magnetic resonance imaging apparatus according to claim 2, wherein the measurement control means alternately repeats two flip angles every repetition of the imaging sequence.

5. The magnetic resonance imaging apparatus according to claim 4, wherein the two flip angles are equal to 70° and 110°.

6. The magnetic resonance imaging apparatus according to claim 1, in the measurement control means executes the imaging sequence every slice in multi-slice imaging.

7. The magnetic resonance imaging apparatus according to claim 6, wherein the measurement control means changes the flip angle of the CHESS pulse when an execution time per slice of the imaging sequence is smaller than a predetermined threshold value.

8. The magnetic resonance imaging apparatus according to claim 1, wherein the measurement control means divides a k space into plural segments, and measures an echo signal belonging to plural segments in the second sequence part.

9. The magnetic resonance imaging apparatus according to claim 8, wherein the measurement control means measures an echo signal every segment in the second sequence part, and also measures a different echo signal every imaging sequence.

10. A magnetic resonance imaging method configured to repeat an imaging sequence comprising a first step of executing a first sequence part configured to suppress a signal from a desired component of an examinee by applying a CHESS pulse, and a second step of executing a second sequence part configured to measure an echo signal from the examinee, thereby measuring an echo signal necessary for image reconstruction of the examinee and reconstructing an image of the examinee by using the echo signal, wherein the flip angle of the CHESS pulses is changed cyclically or randomly at plural times within a plurality of flip angles in the repetition of the imaging sequence in the first step.

11. The magnetic resonance imaging method according to claim 10, wherein in the first step, plural flip angles are cyclically repeated every repetition of the imaging sequence.

12. The magnetic resonance imaging method according to claim 10, wherein in the second step, a k space is divided into plural segments, and an echo signal belonging to plural segments is measured.

* * * * *